United States Patent [19]

Cardoso

[11] Patent Number: 4,898,718

[45] Date of Patent: Feb. 6, 1990

[54] BIOCATALYTIC REACTORS FOR GEL-LIKE AND OTHER TYPES OF IMMOBILIZED BIOCATALYSTS

[75] Inventor: Joaquim P. Cardoso, Sacavem, Portugal

[73] Assignee: Cipan-Companhia Industrial Produtora De Antibioticos, S. A., Lisbon, Portugal

[21] Appl. No.: 20,772

[22] Filed: Mar. 2, 1987

[30] Foreign Application Priority Data

Mar. 19, 1986 [PT] Portugal ..................................... 82225

[51] Int. Cl.$^4$ ............................................... B01J 8/02
[52] U.S. Cl. .................................... 422/211; 422/202; 422/218; 422/220; 422/239; 435/287; 435/288
[58] Field of Search ............... 422/211, 192, 195, 202, 422/211, 218, 220, 238, 239; 435/288, 300, 287; 261/94, 97; 210/150

[56] References Cited

U.S. PATENT DOCUMENTS 4,225,562  9/1980  Anderson ............................ 422/211
4,239,614 12/1980  Hutchings ....................... 422/220 X Primary Examiner—Michael S. Marcus
Assistant Examiner—Rebekah A. Griffith
Attorney, Agent, or Firm—Finnegan, Henderson, Farabow, Garrett, Dunner

[57] ABSTRACT

The present invention provides a new biocatalytic reactor to utilize successfully insoluble biocatalysts to carry out enzymatic reactions. It is especially adequate for the processing of enzymatic reactions using gel-like structure insoluble biocatalysts by eliminating the problems of high pressure drops, microbial contamination and mechanical disintegration which arise when conventional packed columns or agitated tanks are used.

It is also adequate to utilize rigid insoluble biocatalysts to process enzymatic reactions with viscous or particulate substrates.

13 Claims, 5 Drawing Sheets

SUBSTRATE SOLUTION

BIOCATALYTIC REACTORS FOR GEL-LIKE AND OTHER TYPES OF IMMOBILIZED BIOCATALYSTS

BACKGROUND OF THE INVENTION

Field of the Invention

This invention relates generally to a biocatalytic reactor and, more specifically, to a biocatalytic reactor to hold a gel-like insoluble biocatalyst.

A catalyst is a substance that accelerates a chemical reaction and enables it to proceed under milder conditions than otherwise possible. Catalysts are in principle not consumed in the reaction they catalyze.

Biocatalysts are catalysts of biological origin such as enzymes or cells containing enzymatic activity. biocatalysts may be either soluble or insoluble.

An enzyme, a soluble protein with catalytic activity, may become insoluble by linking it to an insoluble carrier, through covalent or weaker bonds, by entrapment in a gel or by cross-linking it with a bifunctional reagent such as for instance glutaraldehyde. In the latter cases a gel-like structure insoluble biocatalyst is obtained to which a particulate form can be conferred by mechanical means.

In order to improve its utilization, cells containing enzymatic activity may also be linked to insoluble supports through covalent or weaker bonds and may be entrapped in gel structures such as, for instance, polyacrylamide, calcium alginate and agar.

In the latter cases a gel-like structure insoluble biocatalyst is obtained to which a particulate form can be conferred by mechanical means.

Particulate insoluble gel-like structures as those obtained for enzymes and cells as described above can be used in a variety of reactors. For example they may be used in a batch stired reactor, a continuous stirred reactor (CSTR), a fixed bed reactor and a fluidized bed reactor.

However, due to the poor mechanical properties, high compressibility and lightness of the gel-like insoluble biocatalysts, it has been found that such insoluble biocatalysts are very difficult to utilize in advantageous conditions. In fact the use of such insoluble biocatalysts in packed columns gives rise to unbearable high pressure drops.

Their use in fluidized bed reactors is precluded due to the small difference between their density and that of the substrate solution.

Lastly their poor mechanical properties also precludes or restricts dramatically their use in batch agitated reactors.

Besides the problems in handling the gel-like structure insoluble biocatalysts, in many catalytic reactions, even with other catalysts there is the need to process very viscous particulate substrate solutions.

Another problem which very often occurs is the heavy contamination of packed beds of insoluble biocatalysts due to its proteinaceous nature.

Thus in view of the numerous disadvantages associated with the use of gel-like structure insoluble biocatalysts and/or viscous or particulate substrate solutions, there has been a long felt need for either a method or an apparatus to facilitate the use of such a catalyst or substrate solutions. The present invention serves that need.

SUMMARY OF THE INVENTION

In our work with gel-like insoluble biocatalysts we have found that the disadvantages associated with their use could be overcome with the use of biocatalytic reactors consisting of a column containing inside a given number of boxes covered with an appropriate wire mesh (baskets) and crossed by a number of void spaces. These void spaces eliminate the problems associated with high pressure drops that develop with packed bed columns and allow a good contact between the insoluble biocatalyst and the substrate solution. Since the insoluble biocatalyst is not subjected to any agitation at all, its mechanical integrity is also preserved. Due to the loose packing of the insoluble biocatalyst, problems of accumulation of microorganisms in the bed of the biocatalyst are also minimized. The processing of viscous or particulate substrate is also facilitated in this type of biocatalytic reactor.

BRIEF DESCRIPTION OF THE DRAWINGS

The object, features and advantages of the present invention will become more fully apparent to those skilled in the art by reference to the following description and examples of the invention.

SPECIFIC EMBODIMENTS

The present invention pertains to the construction of industrial or laboratorial biocatalytic reactors in which the well known concept of hollow fibers has been applied in a macroscopic scale.

Figure 3:
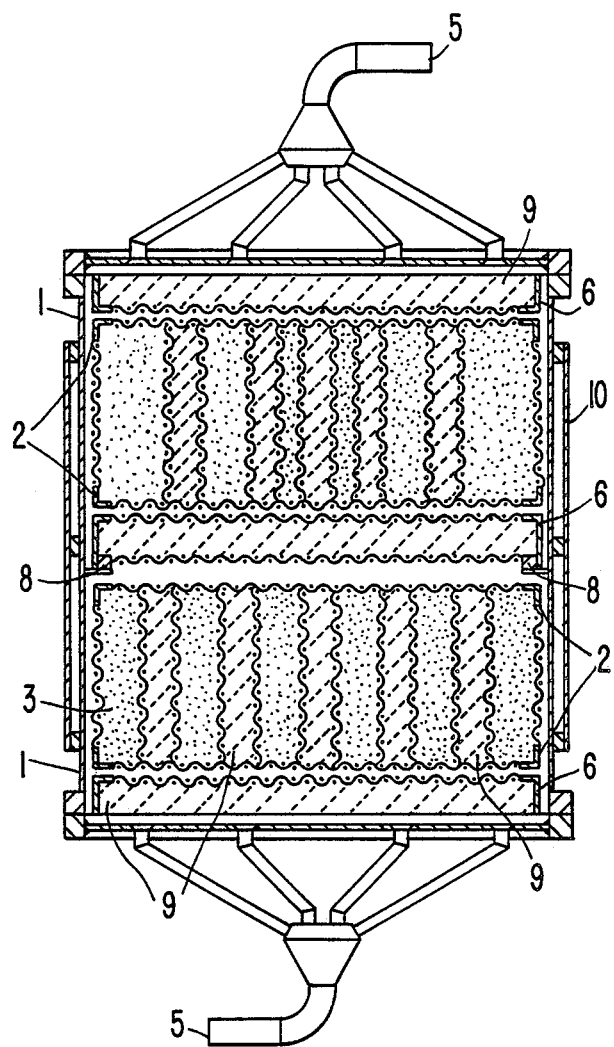
FIG. 3 shows in cross-section a complete biocatalytic reactor made of column 1, two hollow tube type baskets 2, distribution 5 and redistribution substrate system 6. The hollow tubes 4 can also be seen.

The industrial or laboratorial biocatalytic reactors as shown in FIG. 3 are composed of a column 1, within which there is a number of boxes 2, aimed at containing the insoluble catalyst 3, made of a rigid structure supporting a wire mesh cover 2' suitable to prevent the insoluble biocatalyst from escaping, the box and allowing the free passage of the substrate solution.

Besides this feature, each box is crossed from bottom to top by a number of voids shown as hollow tubes 4 in FIG. 3 defined by a wire mesh in their lateral area and bottom and top cross sectional areas which also belong to the box.

These voids allow the free passage of the substrate and at the same time, promote its contact with the insoluble catalyst 3 due to the substrate penetration within the bed of the insoluble catalyst 3 through the wire mesh openings of the voids lateral area.

Figure 1:
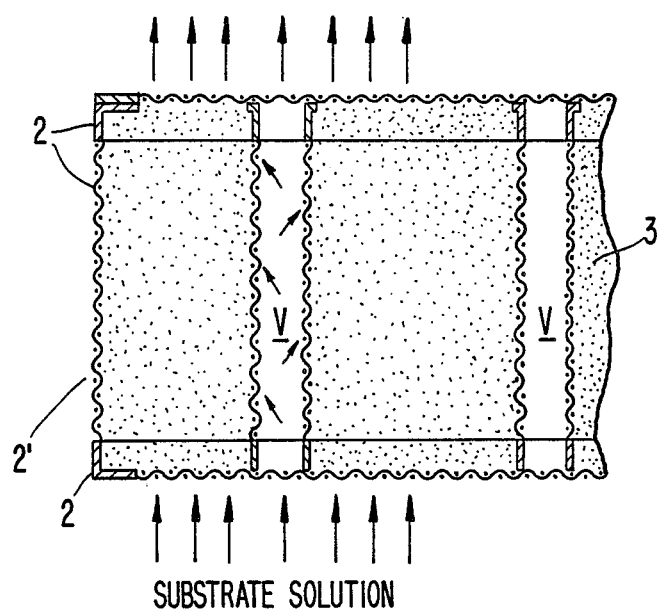
FIG. 1 shows in cross-section the general principle of operation of the object of the present invention where a box 2 the catalyst 3 and the voids V can be seen.

FIG. 1 is a schematic representation of the principle of operation of such a biocatalytic reactor where a box 2 containing the catalyst 3 and the voids V can be seen.

Three types of industrial and laboratory biocatalytic reactors were developed:

(a) Hollow Tube Type Biocatalytic Reactor: In this type of reactor each box (or basket) is crossed from bottom to top by a number of voids spaced-apart tubular each preferably having the form of a tube which allow the free passage of the liquid substrate and at the same time the contact with the insoluble catalyst.

Figure 2A:
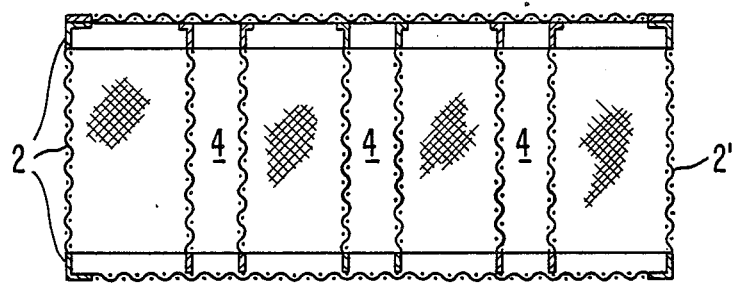
FIG. 2a and 2b shows two cross-sections of a hollow tube type basket 2 containing five cylindrical hollow tubes 4.
Figure 2B:
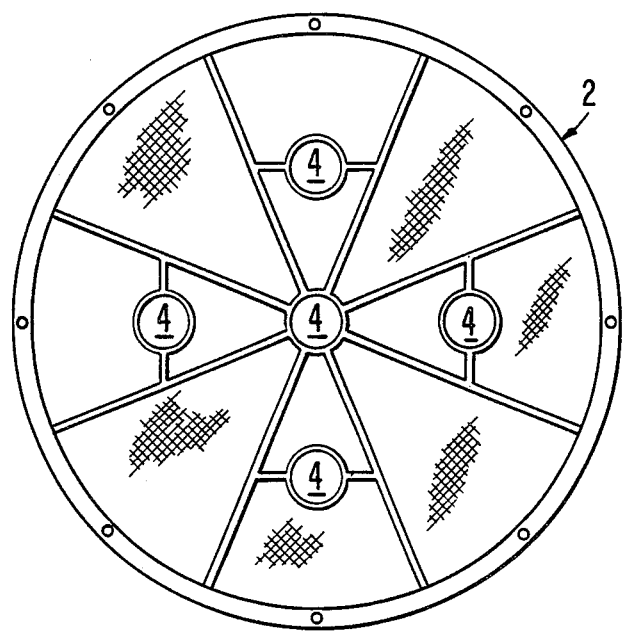

FIG. 2a and 2b underline the principle of functioning of the hollow tube type biocatalytic reactor where a box 2 containing five hollow tubes 4 can be seen.

Referring to FIG. 3 the wire mesh box 2 (or boxes) is contained within a column 1. Through the column distributor 5 the substrate solution is pumped and contacts the insoluble biocatalyst 3 through all the box surface. Part of the flow goes through the voids 4 which have the surface also made of wire mesh and so contacts the insoluble biocatalyst.

The pressure drop through the column 1 is negligible and in certain cases may be increased with some advantage to the contact between catalyst and substrate solution by filling the voids 4 with an inert packing 9 of suitable size. Ceramic materials such as Berl Saddles or Raschig Rings or other equivalent material may be used.

A biocatalytic reactor may be made up of the required number of wire mesh boxes 2 containing the adequate number of voids 4 to allow the proper contact of the substrate solution with the insoluble biocatalyst 3. The optimal ratio between the cross sectional areas of the wire mesh box and of the voids should be between 30 and 50 for the contact to be satisfactory.

To prevent by-passing of the flow, the voids of the precedent box should not be aligned with those of the next box. Also a seal 8 at the end of each box improves the contact of the substrate solution and the insoluble biocatalyst.

FIG. 3 shows schematically a section of an industrial biocatalyst reactor containing two hollow tube-type boxes 2 and the details of the liquid distribution 5 and the redistribution 6 system. The distribution system 5 is made up of several pipes the number of which are a function of the cross-sectional area of the column 1 to be used.

The redistribution system is composed of a number of wire mesh boxes 6 filled with an inert ceramic material 9 and their number exceeds by one the number of hollow tube-type boxes 2 containing the insoluble biocatalyst.

A jacket 10 is also provided to cool or heat the insoluble biocatalyst and therefore the substrate solutions going through the biocatalytic reactor.

A great variety of materials may be used, both for the column and box structures and wire mesh of the boxes or baskets.

Depending on the type and operating conditions of the enzymatic reaction to be carried out construction materials such as stainless steel, carbon steel, copper, plastic materials and others may be used.

(b) Hollow Zone Type Biocatalytic Reactor

In this type of biocatalytic reactor the baskets are crossed from bottom to top by a number of radially spaced annular voids having the configuration of cylindrical zones which allow the free passage of the substract solution and at the same time the contact with the insoluble biocatalyst.

Figure 4A:
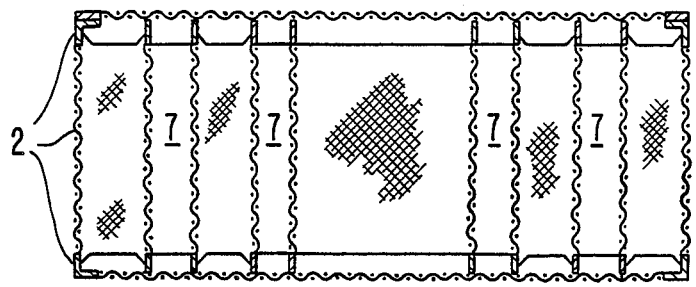
FIG. 4a and 4b show two cross-sections of a hollow zone type basket 2 containing two cylindrical hollow zones 7.
Figure 4B:
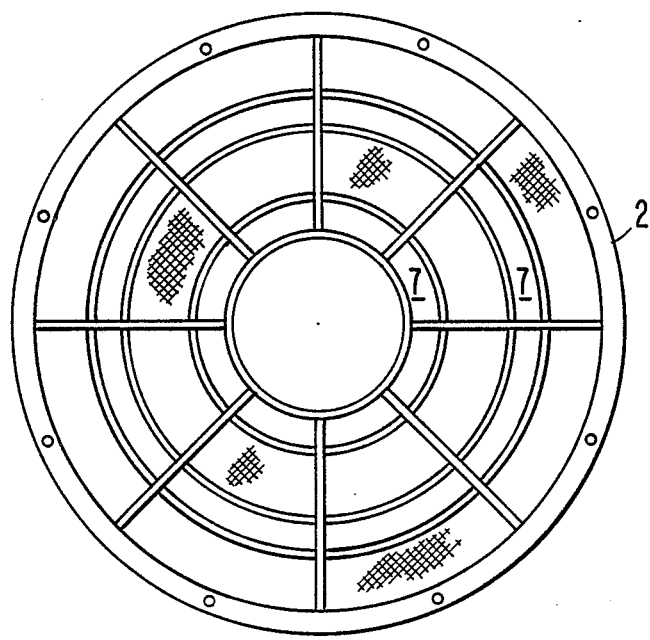

The principle of functioning is equivalent to that of the hollow tube type biocatalytic reactor and FIG. 4a and 4b shows schematically a basket 2 with two hollow zones 7.

The biocatalytic reactors are composed of the necessary number of baskets 2 each containing the appropriate number of hollow zones 7. These should also be filled with inert material to promote the contact between the substrate and the insoluble biocatalyst.

(c) Hollow Tube/Hollow Zone Biocatalytic Reactor

In this type of reactor in each basket there is a combination of voids having the form of tubes and voids having the form of cylindrical zones conferring good contact between the insoluble biocatalyst and the substrate solution and also eliminating pressure drop problems.

The principle of functioning is the same as before.

Figure 5A:
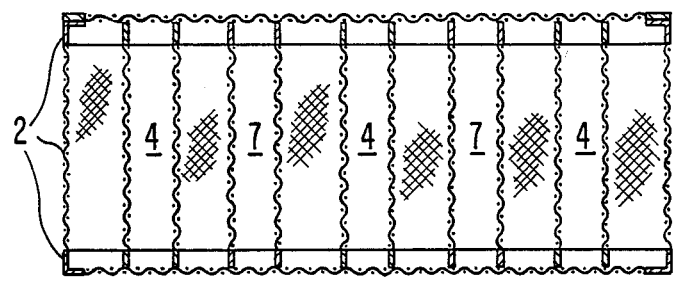
FIG. 5a and 5b show two cross-sections of a hollow tube/hollow zone basket 2 containing five hollow tubes 4 and one cylindrical hollow zone 7.
Figure 5B:
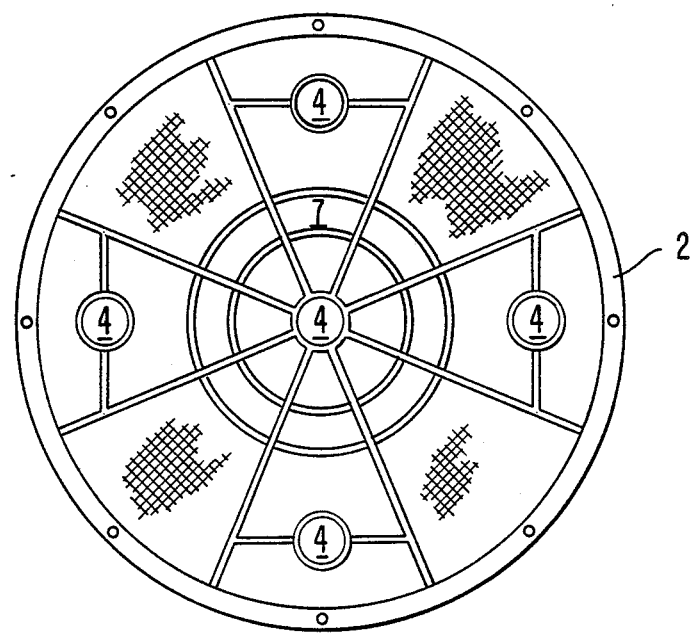

FIG. 5a and 5b are a schematic view of such a type of basket.

In each basket 2 the right combination of hollow tube 4 and hollow zones 7 depends on the cross-sectional area of the baskets.

Having thus disclosed the invention what is claimed is:

1. A biocatalytic reactor for contacting a liquid with a particulate catalyst comprising:
   (a) a column having an inlet and an outlet for said liquid, and
   (b) at least one catalyst containing box inside said column between said inlet and said outlet and extending across the interior of said column, said box having a top end and a bottom end and defined by a wire mesh covering suitable to prevent the catalyst from escaping the box and allowing the free passage of the liquid through it, means defining a plurality of separate voids each free of catalyst material and extending from the bottom end to the top end of said box and defined by wire mesh on their lateral area and top and bottom cross sectional areas.

2. The reactor of claim 1, wherein said voids have a tubular configuration.

3. The reactor of claim 1, wherein said voids have an annular configuration.

4. The reactor of claim 1, wherein a portion of said voids have a tubular configuration and a portion of said voids have an annular configuration.

5. The reactor of claim 1, wherein said column contains a plurality of said boxes, one above the other and the voids of one box are not aligned with the voids of an adjacent box.

6. The reactor of claim 1, further including an inert packing in said voids.

7. The reactor of claim 1, further including distribution means adjacent said inlet and said outlet for distributing and collecting said liquid across the cross sections of said inlet and said outlet, respectively.

8. The reactor of claim 1, further including redistribution means positioned in said column at least at one end of said catalyst containing box and extending across said one end, said redistribution means including at least one wire mesh box for containing an inert material.

9. The reactor of claim 1, further including a jacket means on the wall of said column for heating or cooling said catalyst and said liquid in said reactor.

10. The reactor of claim 1, wherein said plurality of voids include a combination of voids having different configurations.

11. The reactor of claim 1, wherein said column contains a plurality of said catalyst containing boxes, one above the other and the voids of one box are not aligned with the voids of an adjacent box and further including distribution means adjacent said inlet and said outlet for distributing and collecting said liquid across the cross sections of said inlet and said outlet, respectively; redistribution means positioned in said column at one end of said catalyst containing box, said redistribution means including a plurality of wire mesh boxes for containing an inert material, each extending across an end of one of said catalyst containing boxes and containing an inert material.

12. The reactor of claim 11, further including jacket means on the wall of said column for heating or cooling said catalyst and said liquid in said reactor.

13. The reactor of claim 12, further including an inert packing in said voids.

* * * * *